United States Patent [19]

Azria et al.

[11] Patent Number: 4,758,423

[45] Date of Patent: * Jul. 19, 1988

[54] CERTAIN ERGOT PEPTIDE ALKALOIDS ADMINISTERED TO THE NASAL MUCOSA

[75] Inventors: Moise Azria, Paris, France; Thomas Cavanak, Oberwil, Switzerland

[73] Assignee: First Fidelity Bank, National Association, New Jersey, Newark, N.J.

[*] Notice: The portion of the term of this patent subsequent to Jul. 31, 2001 has been disclaimed.

[21] Appl. No.: 871,985

[22] Filed: Jun. 9, 1986

Related U.S. Application Data

[60] Division of Ser. No. 612,137, May 21, 1984, abandoned, which is a division of Ser. No. 328,680, Dec. 8, 1981, Pat. No. 4,462,983, which is a continuation of Ser. No. 194,998, Oct. 8, 1980, abandoned, which is a continuation of Ser. No. 33,242, Apr. 25, 1979, abandoned, which is a continuation of Ser. No. 852,775, Nov. 18, 1977, abandoned.

[30] Foreign Application Priority Data

Nov. 19, 1976 [CH] Switzerland .................. 14575/76
Jun. 7, 1977 [CH] Switzerland .................. 6989/77

[51] Int. Cl.⁴ .............................................. A61K 9/14
[52] U.S. Cl. ................................ 424/45; 514/250
[58] Field of Search ........................ 424/45; 514/250

[56] References Cited

U.S. PATENT DOCUMENTS

| | | | |
|---|---|---|---|
| 3,752,814 | 8/1973 | Fluckiger et al. | 260/268 PE |
| 3,752,888 | 8/1973 | Fluckiger et al. | 424/250 |
| 3,772,299 | 11/1973 | Stadler et al. | 260/268 PE |
| 3,901,891 | 8/1975 | Fehr et al. | 260/268 PE |
| 4,076,715 | 2/1978 | Fehr et al. | 260/285.5 |
| 4,462,983 | 7/1984 | Azria et al. | 424/45 |

OTHER PUBLICATIONS

Bradfield, Curr. Ther., 17, No. 11, 37–40, 1976.
Wilkinson, Brit. Med. J. 1971/2, pp. 754–755.
Graham et al.–New Eng. J. Of Med. 10/20/60, pp. 802–804.
Monthly Index of Med. Specialties (MIMS), 1974, pp. 44, 49 & 50.

*Primary Examiner*—Leonard Schenkman
*Attorney, Agent, or Firm*—Gerald D. Sharkin; Robert S. Honor; Thomas O. McGovern

[57] ABSTRACT

The present invention provides a nasal pharmaceutical composition comprising as active agent a compound of formula I,

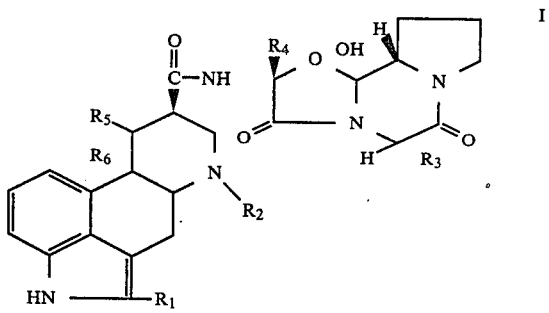

wherein
$R_1$ is hydrogen or halogen,
$R_2$ is hydrogen or alkyl of 1 to 4 carbon atoms,
either (i) $R_3$ is isopropyl, sec-butyl, or isobutyl, $R_4$ methyl, ethyl or isopropyl and $R_5$ hydrogen and $R_6$ is hydrogen or methoxy or $R_5$ and $R_6$ are together a single bond,
or (ii) $R_3$ is benzyl, $R_4$ is methyl, $R_5$ is hydrogen and $R_6$ is hydrogen or methoxy, in association with a pharmaceutically acceptable carrier or diluent, adapted for nasal or pulmonary administration.

13 Claims, No Drawings

CERTAIN ERGOT PEPTIDE ALKALOIDS ADMINISTERED TO THE NASAL MUCOSA

This is a division of application Ser. No. 612,137, filed May 21, 1984 now abandoned, which in turn is a division of application Ser. No. 328,680, filed Dec. 8, 1981, now U.S. Pat. No. 4,462,983, which in turn is a continuation of application Ser. No. 194,998, filed Oct. 8, 1980, now abandoned, which in turn is a continuation of application Ser. No. 33,242, filed Apr. 25, 1979, now abandoned, which in turn is a continuation of application Ser. No. 852,775, filed Nov. 18, 1977, now abandoned.

This invention relates to ergot peptide alkaloids.

The present invention provides a nasal pharmaceutical composition comprising as active agent a compound of formula I,

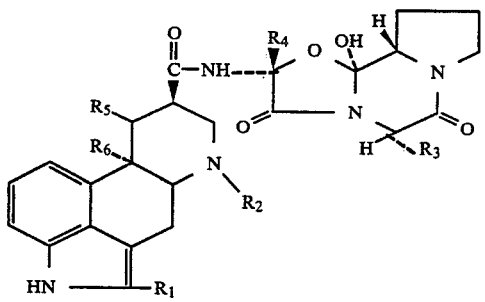

wherein
$R_1$ is hydrogen or halogen,
$R_2$ is hydrogen or alkyl of 1 to 4 carbon atoms,
either (i) $R_3$ is isopropyl, sec-butyl, or isobutyl, $R_4$ methyl, ethyl or isopropyl and $R_5$ is hydrogen and $R_6$ is hydrogen and methoxy or $R_5$ and $R_6$ are together a single bond,
or (ii) $R_3$ is benzyl, $R_4$ is methyl, $R_5$ is hydrogen and $R_6$ is hydrogen or methoxy,
in association with a pharmaceutically acceptable carrier or diluent, adapted for nasal administration.

Satisfactory formulations may be formed in conventional manner. The exact formulation will naturally depend on inter alia the active agent used, and the carrier or diluent used. Nasal compositions comprise an aqueous solution, conveniently containing a viscosity-increasing agent such as methyl cellulose. Such liquid compositions may be in an atomiser or a container adapted to provide drops. The compounds may be in solid form and have a particle size of up to 10 microns in diameter, preferably 0.5 to 5 microns. The carrier or diluent may be lactose, which may comprise 87.5 to 97.5% of the total weight, in a hard capsule, via an insufflator, e.g. for nasal administration.

The composition may be in the presence of a pharmaceutically acceptable propellant such as a halogenated hydrocarbon and may be in a closed container under pressure. The container may be adapted to deliver a discrete dosage, e.g. from 0.1 to 5 mg of the compound. The container may be an aerosol.

The present invention also provides a nasal applicator containing as active agent a compound of formula I.

The applicator may be any conventional applicator for administering an active agent to the nose. Generally, a dry or liquid spray is produced by such an applicator, which may, for example, be:

(a) an aerosol
(b) a liquid spray device or drop device for nasal administration, or
(c) a powder spray device The applicator may be adapted to provide a unit dosage of the active agent.

Various forms of applicators and compositions therefor will now be discussed.

(1) Any aerosol device which produces a spray may be used, e.g. a nebulizer. For example, spraying by means of ultrasonic aerosol appliances or by means of propellant gas pressure bottles is preferred. In this instance, the active agents are conveniently present in the form of solutions or suspensions.

If an ultrasonic aerosol appliance is used, the active agent is conveniently present as a solution. These solutions may be obtained by dissolving the active agent in a mixture of ethanol and water and conveniently adding to the resulting solution isotonizing additives, such as sodium chloride, and buffer substances, such as acetate buffer. The amount of active agent ranges conveniently from 0.1 mg to 5 mg/ml. The water/ethanol mixture used as solvent contains conveniently water and ethanol as a ratio of from 98:2 and 80:20, preferably 90:10, (by volume) respectively. Other additives used in order to obtain isotonia and buffering substances should be present at an amount totalling 1% or less by weight relative to the total solution. Furthermore, it is possible to add stabilizers, such as sodium pyrosulfite, ascorbic acid, etc., as well as flavouring substances, e.g. menthol, also at amounts of at most 1% by weight related to the total solution.

If the active agent is to be sprayed by means of propellant gas pressure bottles, it is possible to use the solutions described for the use in ultrasonic aerosol appliances. These solutions may be added to compressed propellant gases, for example, fluorinated and/or chlorinated hydrocarbons, e.g. trichlorofluoromethane (Frigen 11), dichlorodifluoromethane (Frigen 12), trichlorotrifluoroethane (Frigen 113) or dichlorotetrafluoroethane (Frigen 114).

In place of the solutions in propellant gas pressure bottles, suspensions of the micronized active agent in the compressed propellant may be used. In this case, it is convenient to add a tenside, for example, Tween 80, or polyethyleneglycol esters of fatty acids, especially sorbitane monooleate, etc. The amount of active agent may be 1 to 10% by weight and the amount of tenside 0.1 to 1% by weight related to the total amount of the suspension, including the propellant.

(2) To produce a nasal spray or nasal drops, the composition may comprise the active agent in water, buffering substances, e.g. acetate buffer, isotonizing additives, e.g. sodium chloride, preservatives, e.g. Nipakombin, solution aids, e.g. polyethylene glycol 400, viscosity-increasing agents, e.g. methyl cellulose, etc. The solutions may be in an atomiser, a spray appliance, or a nasal pipette. The amount of weight of the active agent in these solutions should be 1 to 10% by weight, and of the other additives, approximately 0.1 to 1% by weight related to the total amount of the solution. Instead of a solution, emulsions of the active agents in mono- and/or polyvalent alcohols, for example triethylene glycol/ethanol, polyethylene glycol 300–400/ethanol, propylene glycol/ethanol, but also in a mixture of water and mono- and/or polyvalent alcohols, e.g. water/ethanol, water/polyethylene glycol 300–400 may be used. The preferred amounts of the individual components in the solvent mixture are described in Example 3. In the latter, the active agent should be present at an amount of 0.5 to 5% by weight related to the total amount. Furthermore, oils such as sesame oil, paraffin oil, etc., in order to obtain the organic phase as well as tensides (emulsifying agents), e.g. sorbitane monooleate, totalling up to 1% by weight, may be present during the production of emulsions.

The emulsion is conveniently administered by means of atomisers, plastic bottles each equipped with a nozzle or, after adding propellant gas, in pressure packs, the active agent in solution forming an emulsion with the liquified propellant gas upon the addition of the liquified gas.

(3) For a nasal powder spray, the active agent may be present in micronised from, e.g. of particle diameter less than 10 microns, e.g. 2 to 10 microns, mixed together with micronised and non-micronised lactose. The weight ratio of the active agent to the lactose may be 0.25:12.5% to 99.75:87.5%. The mixture may be filled into hard gelatine capsules (fill weight 20-40 mg per capsule) and sprayed in conventional manner, for example by means of a suitable insufflator.

The present invention also provides a method for treating an animal with a compound of formula I defined above which comprises administering locally the compound to the nasal mucous membranes.

In formula I, if $R_2$ signifies an alkyl group, this may especially be methyl or isopropyl. If $R_1$ signifies halogen, this signifies fluorine, chlorine, bromine or iodine, especially bromine.

Preferred representatives of the compounds of formula I are dihydroergocristine, α- or β-dihydroergocryptine, dihydroergocornine, which are preferably used in the form of a mixture known as dihydroergotoxin, bromocriptine, dihydroergotamine and dihydroergonine. The compounds of formula I may be used in the free base form or in acid addition salt forms, for example the methanesulphonate, maleate or tartrate.

It has been found that the nasal compositions, when administered locally to the mucous membranes in the nose or the lungs in phencyclidine-anaesthetised rhesus monkeys, lead to a notable peak blood concentration of the compounds and/or a short onset time to peak blood concentration of the compounds on administration of, for example, 1 to 10 mg of the compound. The concentration of the compound in the blood may be measured by conventional radioimmunoassay, e.g. according to the principles of J. Rosenthaler and H. Munzer, Experientia 32, 234 (1976).

For this administration, the dosage will, of course, vary depending on the compound employed, mode of administration and treatment desired. However, in general, satisfactory results are obtained when administered at a daily dosage of from about 0.001 to about 0.1 mg per kg animal body weight, conveniently given in divided doses 2 to 5 times a day or in sustained release form. For the larger mammals, the total daily dosage is in the range from about 0.1 to about 10 mg.

The present invention therefore provides a method of treating animals with a compound of formula I, as defined above, which comprises administering a therapeutically effective amount of a compond of formula I for local administration to the nasal membranes of an animal in need of such treatment.

In the following Examples, all percentages, unless otherwise indicated, refer to parts by weight. Nipakombin means a 67:33 mixture of p-hydroxybenzoyl methyl ester and p-hydroxybenzoyl propyl ester. Tween 80 is polyethylene (20) sorbitan monooleate (I.C.I. England). Frigen 113 is trichlorotrifluoroethane. Frigen 11/12/114 is a 25:50:25 (by volume) mixture of trichlorofluoromethane, dichlorodifluoromethane and dichlorotetrafluoroethane.

EXAMPLE 1 Dihydroergotamine Solution Aerosol

Basic Composition

| Dihydroergotamine methanesulphonate | 25 mg |
| Ethanol (94%) | 520 mg |
| Water (distilled) | 120 mg |
| Frigen 11/12/114 | 1000 mg |

Production

The dihydroergotamine, ethanol and water are mixed to give a solution. The solution is filled into an aerosol bottle. A valve outlet is fitted and crimped to seal the bottle. The required amount of propellant is added through the valve.

EXAMPLE 2 Dihydroergotamine Suspension Aerosol

Basic Composition

| Dihydroergotamine methanesulphonate micronised particle diameter <10μ | 200 mg |
| Tenside: | |
| Sorbitan monooleate or Soya bean lecithin | 20 mg |
| Frigen 113 | } to 1 ml |
| Frigen 11/12/114 | |

Production

The dihydroergotamine is triturated with the tenside in the presence of a little Frigen 113 in a cooled mortar. Further Frigen 113 is added to give a homogenous mixture, if necessary using a polytron. The mixture is filled into aerosol bottles while stirring and cooling continuously. A valve outlet is fitted and crimped to seal the bottle. The required amount of propellant gas is then added through the valve.

EXAMPLE 3

Dihydroergotamine 2-Phase Aerosol Emulsion

Basic Composition

| Dihydroergotamine methanesulphonate | 50 mg |
| Sorbitan monooleate | 5 mg |
| Ethanol (absolute) | 100 mg |
| Glycol such as Triethylene glycol, propylene glycol, Polyethylene glycol (MW 300-400) | 1 ml |
| Frigen 11/12/114 | q.s. |

If desired, the glycol may be replaced by ca. 200-300 mg water.

Production

Analogous to Example 1.

EXAMPLE 4

Dihydroergotamine Nasal Liquid Spray Applicator

Basic Composition

| | 4A | 4B | 4C | 4D |
| --- | --- | --- | --- | --- |
| Dihydroergotamine methanesulphonate | 1.85% | 1.85% | 1.85% | 1.85% |

|  | 4A | 4B | 4C | 4D |
|---|---|---|---|---|
| Nipakombin | 0.08% | 0.08% | 0.08% | — |
| Sodium acetate trihydrate | 0.168% | 0.168% | 0.168% | 0.168% |
| Glacial acetic acid | 0.42% | 0.42% | 0.42% | 0.42% |
| Methyl cellulose | — | 0.5% | 0.5% | 1.0% |
| Polyethylene glycol 400 | — | — | 10% | 10% |
| Tween 80 | — | — | — | 0.1% |
| Chlorohexidine diacetate | — | — | — | 0.01% |
| Ethanol (94%) | 15% | 15% | 15% | 15% |
| Water | to 100% | to 100% | to 100% | to 100% |

Production

The ingredients without the dihydroergotamine and with some of the water are mixed together. The dihydroergotamine is then added, and the mixture completed by addition of water. The resulting solution may be made isotonic, if desired, by the addition of sodium chloride, mannitol or sorbitol, etc., and is filled into a nasal spray applicator, e.g. an atomiser.

EXAMPLE 5

Dihydroergotamine Powder Spray Applicator

A mixture of micronised dihydroergotamine methanesulphonate with lactose is filled into a gelatine capsule.

For nasal application, the contents are administered by spraying into the nostril by means of a rubber bulb or other atomiser.

EXAMPLE 6

Bromocriptine Suspension Aerosol

Basic Composition

|  | Wt. per dose |
|---|---|
| Bromocriptine methanesulphonate | 1.324 mg |
| Soya bean lecithin | 0.2 mg |
| Absolute ethanol | 3 mg |
| Frigen 113 | 13.5 mg |
| Frigen 11/12/114 | 47.50 mg |

Production

A composition containing 90 such doses is prepared in analogous manner to that described in Example 2.

EXAMPLE 7

Bromocriptine Nasal Liquid Spray

Basic Composition

|  | 7A mg | 7B mg | 7C mg |
|---|---|---|---|
| Bromocriptine methanesulphonate | 8.63 | 8.63 | 2.87 |
| Ascorbic acid | 0.50 | 0.5 | — |
| Glacial acetic acid | to pH 2.9 | to pH 2.9 | 1.55 |
| Sodium acetate | — | — | 1.02 |
| Mannitol | 50 | 50 | 45 |
| Methyl cellulose | — | 10 | — |
| Ethanol (94%) | 120 | 120 | — |
| Water | to 1.00 ml | to 1.00 ml | to 1.00 ml |

Production

A 14 ml bottle fitted with a piston spray device is filled with the above composition in a $CO_2$ atmosphere.

Compositions may be made using dihydroergonine or dihydroergotoxin in appropriate amounts instead of dihydroergotamine in Examples 1 to 5 or bromocriptine in Examples 6 and 7.

What is claimed is:

1. A pharmaceutically acceptable nasal spray applicator consisting essentially of a nasal applicator containing therein an ergot peptide alkaloid composition for nasal administration comprising per unit dose a therapeutically effective amount of dihydroergocristine or an ergot peptide alkaloid of the formula

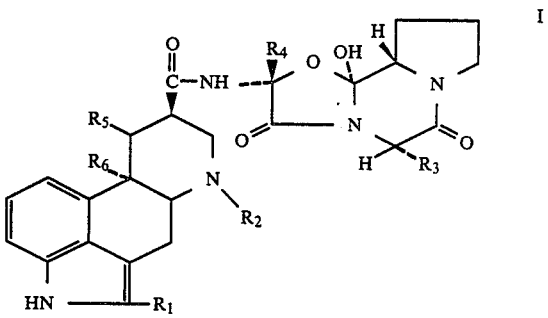

wherein
   $R_1$ is hydrogen or halogen,
   $R_2$ is hydrogen, methyl or isopropyl, and
   either (i) $R_3$ is isopropyl, sec-butyl or isobutyl, $R_4$ is methyl, ethyl or isopropyl, and $R_5$ is hydrogen and $R_6$ is hydrogen and methoxy or $R_5$ and $R_6$ are together a single bond,
   or (ii) $R_3$ is benzyl, $R_4$ is methyl, $R_5$ is hydrogen and $R_6$ is hydrogen or methoxy,
or a pharmaceutically acceptable acid addition salt thereof, in association with a pharmaceutically acceptable carrier suitable for nasal spray administration, said nasal applicator being adapted to administer a unit dose of the ergot peptide alkaloid to the mucous membrane of the nose.

2. A pharmaceutically acceptable nasal spray applicator as claimed in claim 1 wherein the composition comprises per unit dose 0.1 to 5 mg of the ergot peptide alkaloid.

3. The nasal spray applicator as claimed in claim 1 wherein the compound of formula I is dihydroergotamine.

4. The nasal spray applicator as claimed in claim 1 wherein the compound of formula I is bromocriptine.

5. The nasal spray applicator as claimed in claim 1 wherein the compound of formula I is dihydroergotoxine.

6. The nasal spray applicator as claimed in claim 1 adapted to administer 0.1 to 5 mg of the ergot peptide alkaloid per administration.

7. A nasal spray applicator according to claim 1 in which the ergot peptide alkaloid composition is in liquid form.

8. The nasal spray applicator as claimed in claim 7 wherein the ergot alkaloid composition contains 0.1 to 5 mg of active agent per ml of solution.

9. A nasal spray applicator according to claim 7 in which the ergot peptide alkaloid composition contains a propellant acceptable in nasal administration.

10. A nasal spray applicator according to claim 9 in which the propellant is a halogenated hydrocarbon.

11. A nasal spray applicator according to claim 7 in which the ergot peptide alkaloid composition is in the form of an aqueous solution containing a viscosity increasing agent.

12. A nasal spray applicator according to claim 11 in which the viscosity increasing agent is methyl cellulose.

13. A nasal spray applicator according to claim 7 in which the carrier is a non-aqueous solvent.

* * * * *